United States Patent [19]

Haber et al.

[11] Patent Number: 5,300,041
[45] Date of Patent: Apr. 5, 1994

[54] DOSE SETTING AND REPEATING SYRINGE

[75] Inventors: Terry M. Haber, Lake Forest; William H. Smedley, Lake Elsinore; Clark B. Foster, Laguna Niguel, all of Calif.

[73] Assignee: Habley Medical Technology Corporation, Laguna Hills, Calif.

[21] Appl. No.: 893,417

[22] Filed: Jun. 1, 1992

[51] Int. Cl.$^5$ .............................. A61M 5/00
[52] U.S. Cl. ........................ 604/207; 604/211; 604/218; 604/232
[58] Field of Search .................. 604/207–211, 604/186, 187, 218, 219, 220, 232; 222/325, 326, 327, 391, 137

[56] References Cited

U.S. PATENT DOCUMENTS

| | | | |
|---|---|---|---|
| 4,865,591 | 9/1989 | Sams | 604/209 X |
| 4,936,833 | 6/1990 | Sams | 604/209 X |
| 5,017,190 | 5/1991 | Simon et al. | 604/207 |
| 5,092,842 | 3/1992 | Bechtold et al. | 604/209 X |

*Primary Examiner*—John D. Yasko
*Attorney, Agent, or Firm*—Townsend & Townsend Khourie & Crew

[57] ABSTRACT

A dose setting and repeating syringe (2) allows the user to simply and accurately make a series of injections, each of the same dose. The syringe includes a dose programming assembly which permits the dose for each injection to be preset by limiting the distance the piston (16) housed within the barrel (4) of the syringe moves. This can be done in various ways, such as mechanically, using a ratchet assembly (22, 28), or hydraulically, using a generally conventional cartridge (92) containing the pharmaceutical. A user-actuated dose plunger (40) is connected to the piston (16) and is used to drive the piston down the barrel. The axial movement of the dose plunger, and thus the dose dispensed, depends on the axial position of a dose ring (52) threaded to the proximal end (12) of the barrel.

12 Claims, 10 Drawing Sheets

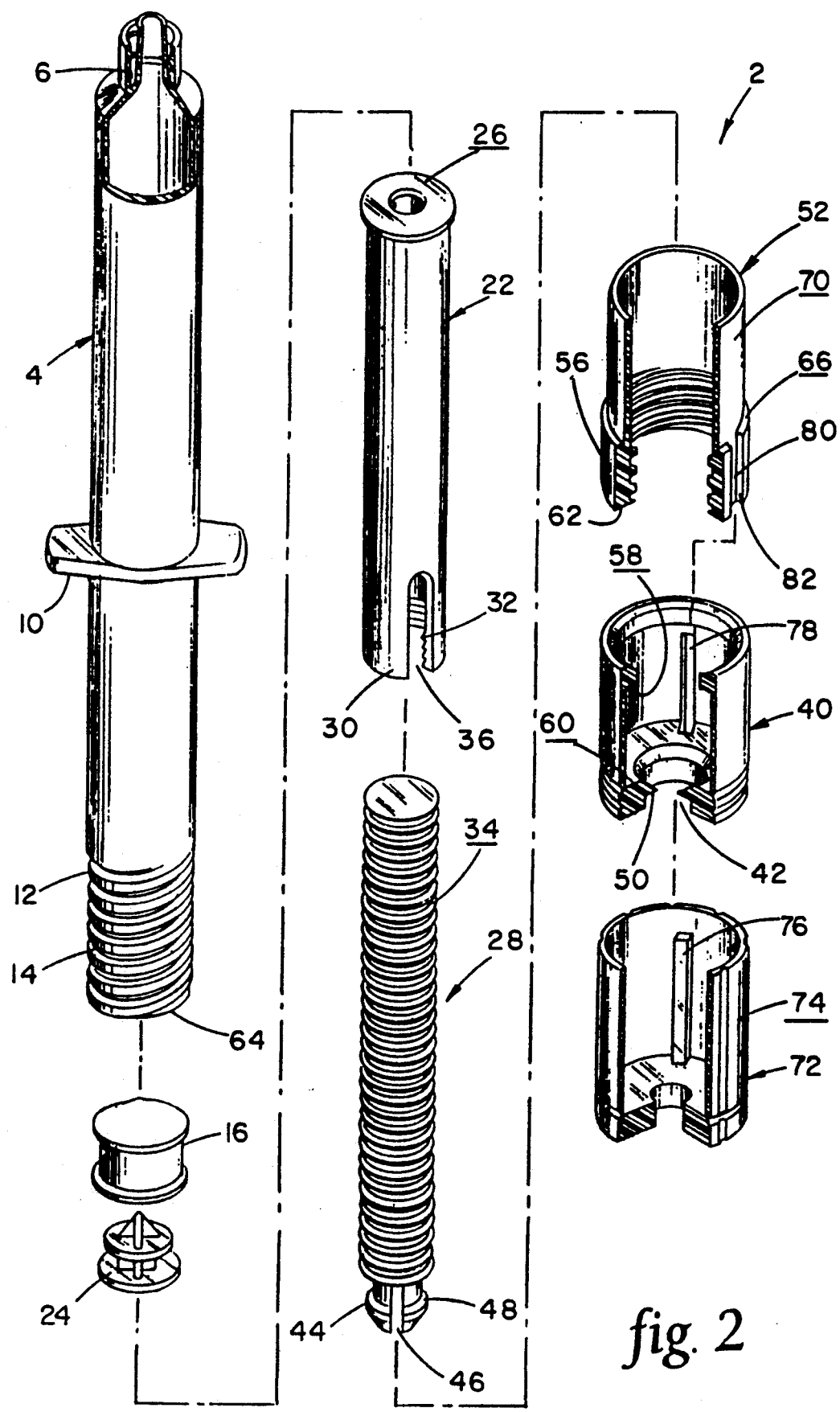

DOSE SETTING AND REPEATING SYRINGE

This application relates to U.S. patent application Ser. No. 07/628,271, filed Dec. 14, 1990, now abandoned, and U.S. patent application Ser. No. 07/808,717, filed Dec. 17, 1991 now U.S. Pat. No. 5,240,146.

BACKGROUND OF THE INVENTION

Patients, particularly diabetic patients, often need to use drug self-delivery systems which are operated by the user for routine medication injections during in-home use. Diabetics must often rely on insulin delivery systems which can be used at home or at work to administer necessary insulin. These self-delivery systems must be safe, accurate in dose measurement and easy to use. Conventional syringe devices have been used in the past but place the burden of accuracy for the dose measurement upon the user.

Every diabetic patient is different and may require direct and continued medical supervision. The patient, however, is commonly instructed by the physician as to the strength, type, amount and times at which insulin must be injected on a self-injection basis. The accuracy of the dose of insulin, therefore, is extremely important. Hypoglycemia, commonly referred to as insulin reaction, can occur when the blood glucose level falls very low. Such an event can happen if a diabetic patient delays or misses a meal, exercises at a higher level or for a longer duration than usual without eating or takes too much insulin.

In contrast, not enough insulin may result in diabetic ketoacidosis. Such a condition can create loss of appetite, thirst, drowsiness, illness or infection. In severe cases, a diabetic coma can result.

Obviously, the failure to administer accurate doses of insulin can be extreme. Therefore, diabetic patients can benefit from a reliable and accurate dose setting syringe which provides pre-programmed dose amounts to furnish repetitive and consistent doses of insulin or other medication.

SUMMARY OF THE INVENTION

The present invention relates to a dose setting and repeating syringe device which allows repetitive injection of a pre-programmed dose amount from a volume of insulin or other pharmaceutical contained within the syringe.

In one preferred embodiment of the invention, the device is configured as a non-reusable syringe having a mechanical dose programming assembly. In this embodiment, a hollow barrel is provided having a needle or distal end and an open proximal end. A piston is housed within the hollow barrel and defines a pharmaceutical chamber between the piston and the needle end. A mechanical dose programming assembly, coupled to the proximal end of the hollow barrel, includes a dose ring and a dose plunger slidably mounted onto the dose ring and coupled to a ratchet stem. The dose ring is threadably mounted onto the proximal end of the hollow barrel and provides adjustable programming of sliding travel of the dose plunger relative to the hollow barrel. The ratchet stem is engaged by a ratchet plunger which is activated to drive the piston in the proximal to needle end direction and thereby displace a desired amount of the contents of the pharmaceutical chamber through the needle end of the hollow barrel. Because the dose plunger is coupled to the ratchet stem, sliding travel of the dose plunger moves the ratchet stem. The ratchet stem and ratchet plunger telescope in a ratcheting action whereby movement of the dose plunger in the proximal to needle end direction is directly communicated to the piston through the ratchet plunger. Return stroke movement of the dose plunger, in the needle end to proximal direction, ratchets the ratchet stem away from the ratchet plunger in the same direction without changing the position of the ratchet plunger within the hollow barrel. In this way, the piston can be driven in the proximal to needle end direction to discharge a portion of the contents of the pharmaceutical chamber and prevent movement of the piston in the reverse direction, that is, in the needle end to proximal direction. Thus, in this embodiment, the syringe device is intended to be non-reusable.

An advantage of the invention is that the dose of medication contained in pharmaceutical chamber can be programmed by the user by adjusting the threaded engagement of the dose ring along the hollow barrel. By adjusting the position of the dose ring along the hollow barrel, the relative available travel of dose plunger is programmed. By programming the available travel, the user can accurately program the dose or amount of medication administered for each injection stroke of the syringe device.

The invention can be made so that adjustments of the dose ring requires the use of a special adapter or dose setting key. This key can be retained by the physician if there is a perceived need to control the dose.

The syringe is operated using an action similar to a conventional needle syringe by placing fingers on finger ledges which extend outwardly from the dose barrel. The user's thumb is used to push on the dose plunger in the proximal to needle end direction to facilitate injection of the pharmaceutical. As the thumb drives the dose plunger towards the needle end, the ratchet stem travels along with the dose plunger and in turn forces the ratchet plunger against the piston which is also displaced in the proximal to needle end direction. During the return stroke, the dose plunger is pulled in the needle end to proximal end direction which ratchets the ratchet stem away from the ratchet plunger and the piston. Repeated stroke and return stroke action provides accurate pre-programmed equal dosage amounts for each injection. The syringe thereby provides a pre-programmed measurement of pharmaceutical for each injection.

An alternative embodiment of the invention uses a hydraulic dose programming mechanism and replaceable pharmaceutical cartridges for reusable applications. In this embodiment, the syringe device includes a syringe barrel configured to receive a removable cartridge slidably positioned in the syringe barrel. The open needle end of the cartridge mates with a piston having an integral check valve. The cartridge includes a cartridge barrel and a floating piston positioned within the cartridge barrel. Liquid insulin or other pharmaceutical is contained within the cartridge between the piston check valve and the floating piston. Another check valve is secured to the syringe barrel at the tip end of the syringe barrel. When the cartridge is fully inserted in the syringe barrel, a variable volume pharmaceutical chamber is created between the tip check valve and the piston check valve mated to the cartridge. The combination of the two check valves and the movable piston provides for one-way flow of pharmaceutical from the cartridge into the variable volume chamber when the cartridge is pulled proximally and out through the needle assembly when the cartridge is pushed distally.

A dose ring, similar to that described in the first embodiment, is threadably engaged to the proximal end of the barrel. A dose plunger is slidably engaged with the dose ring as also previously described. The dose plunger is secured to the proximal end of the cartridge so that reciprocal movement of the dose plunger causes like movement of the cartridge. Adjustment of the threaded engagement between the dose ring and the barrel allows programmed adjustment of the travel available for the dose plunger and thus adjustment of the amount of medication injected during each stroke.

Using the thumb or finger, the user depresses the dose plunger in the proximal to needle end direction. During this movement, the dose plunger drives the cartridge in the same direction. This displacement causes the stopper check valve to move towards the tip check valve and therefore displace any air or liquid within the variable volume pre-injection chamber, out through the tip check valve and through the Luer lock tip and needle cannula mounted thereto. On a return stroke, the dose plunger is returned to a pre injection position by movement in the needle tip to proximal direction. The dose plunger includes a cartridge seat which frictionally engages the cartridge and pulls the cartridge in the same direction, thereby increasing the volume of the variable volume chamber. Due to the one-way flow structure described, the increasing volume creates a partial vacuum in the chamber, thereby hydraulically drawing contents from the cartridge into the variable volume pre-injection chamber as the volume of the variable volume chamber increases. This hydraulic pressure also draws down the floating piston within the cartridge in the proximal to distal direction a distance proportional to the volume of cartridge contents moving into the variable volume chamber. An injection stroke of the dose plunger again displaces the pharmaceutical through the Leur lock tip and out through the needle cannula.

Repeat application of the injection and return strokes on the dose plunger provides equal dose injections for each injection stroke. The amount of liquid in each dose can be accurately metered and controlled using the dose plunger, dose ring, and removable dose-setting key as previously described. A dose setting key can also be provided to lock the threaded position of the dose ring onto the barrel if desired. This could be achieved by using a dose setting key with a relatively deep (radially inwardly extending) key element. The key element could pass through axially extending slots formed in the dose plunger and the dose ring to engage an axial groove formed in the threads on the barrel to prevent the dose ring from rotating relative to the barrel.

In either the mechanical embodiment or the hydraulic embodiment, the present invention provides an accurate dose setting device which allows repetitive and repeated administration of pre-programmed doses from the same syringe without resetting the dose amount at each injection. The device is light weight, convenient, accurate and provides enhanced confidence and convenience for the user over prior art devices.

Other features and advantages of the invention will appear from the following description in which the preferred embodiments have been set forth in detail in conjunction with the accompanying drawings.

BRIEF DESCRIPTION OF THE DRAWINGS

FIG. 2 is an exploded perspective view of the component parts of the device shown in FIG. 1;

DESCRIPTION OF THE PREFERRED EMBODIMENT

Figure 1:
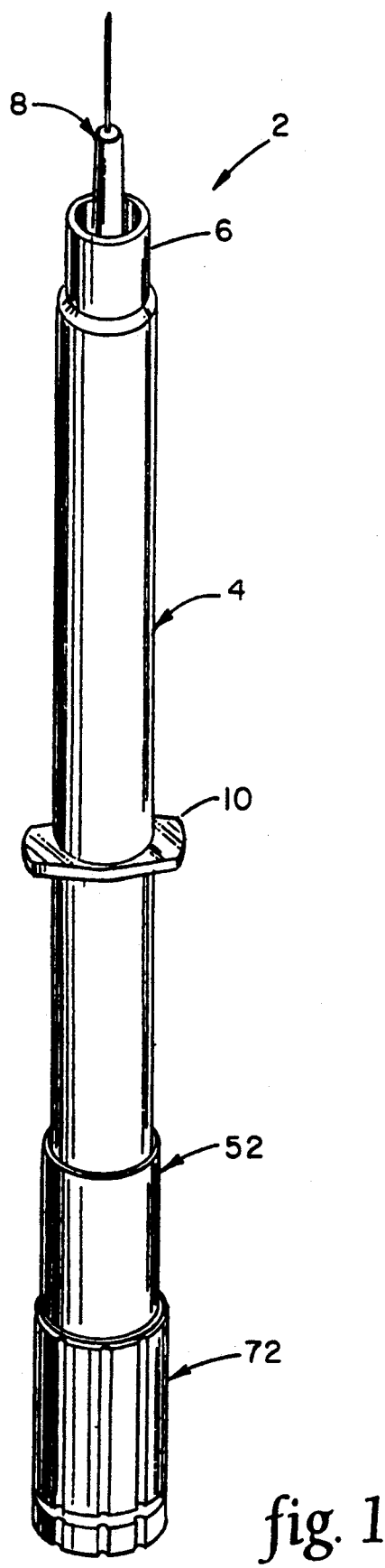
FIG. 1 is a perspective view of a preferred embodiment of the invention having a mechanical dose repeating assembly.

FIGS. 1-3C illustrate a first embodiment of a dose setting and repeating syringe 2 made according to the invention. Syringe 2 includes an elongate, hollow barrel 4 having a needle end 6 configured to accept a needle assembly 8 using a Luer lock type of securing mechanism, as is conventional. Barrel 4 also includes finger ledges 10 extending radially outwardly from the barrel midway along the length of the barrel. The proximal end 12 of barrel 4 has external threads 14, the use of which is discussed below.

A piston 16 is housed within the interior 18 of barrel 4 and is adapted to move axially along the interior. Piston 16 is driven in the distal direction, that is in the direction of arrow 20, by a ratchet plunger 22 through an insert 24. Insert 24 is secured to plunger face 26, such as using an adhesive, so that ratchet plunger is securely connected to piston 16. Piston 16 is sized to provide a sufficient frictional engagement with the inside surface of barrel 4 to ensure proper ratcheting action.

Ratchet plunger 22 is hollow and is sized to accept an elongate ratchet stem 28 through its open end 30. Open end 30 has a number of ratchet teeth 32 formed within the interior of plunger 22 which engage the serrated outer surface 34 of ratchet stem 28. Open end 30 has a plunger slit 36 which permits open end 30 to dilate during the ratcheting action between ratchet stem 28 and ratchet plunger 22. That is, ratchet teeth 32 and serrated outer surface 34 are sized and configured so that movement of ratchet stem 28 in the direction of arrow 20, that is distally, drives ratchet plunger 22 and piston 16 therewith in the direction of arrow 20 so to drive the pharmaceutical 37 housed within interior 18 of barrel 4 out through needle end 6 and needle assembly 8. After an injection, movement of ratchet stem 28 in a proximal direction, that is in the direction of arrow 38, causes a ratcheting action between teeth 32 and surface 34 so that ratchet plunger 22 and piston 16 remain in place within barrel 4.

This reciprocal movement of ratchet stem 28 is achieved by manipulation of a cupped-shaped dose plunger 40. Dose plunger 40 has an opening 42 at its proximal end which accepts a proximal end 44 of ratchet stem 28. Proximal end 44 includes an axially oriented slot 46 which permits proximal end 44 to be forced through opening 42 and then expand outwardly so that a collar 48 formed at proximal end 28 engages a collar ledge 50 formed at opening 42. This connection allows dose plunger 40 to rotate freely relative to ratchet stem 28 but causes ratchet stem 28 to move axially with the dose plunger.

Figure 3A:
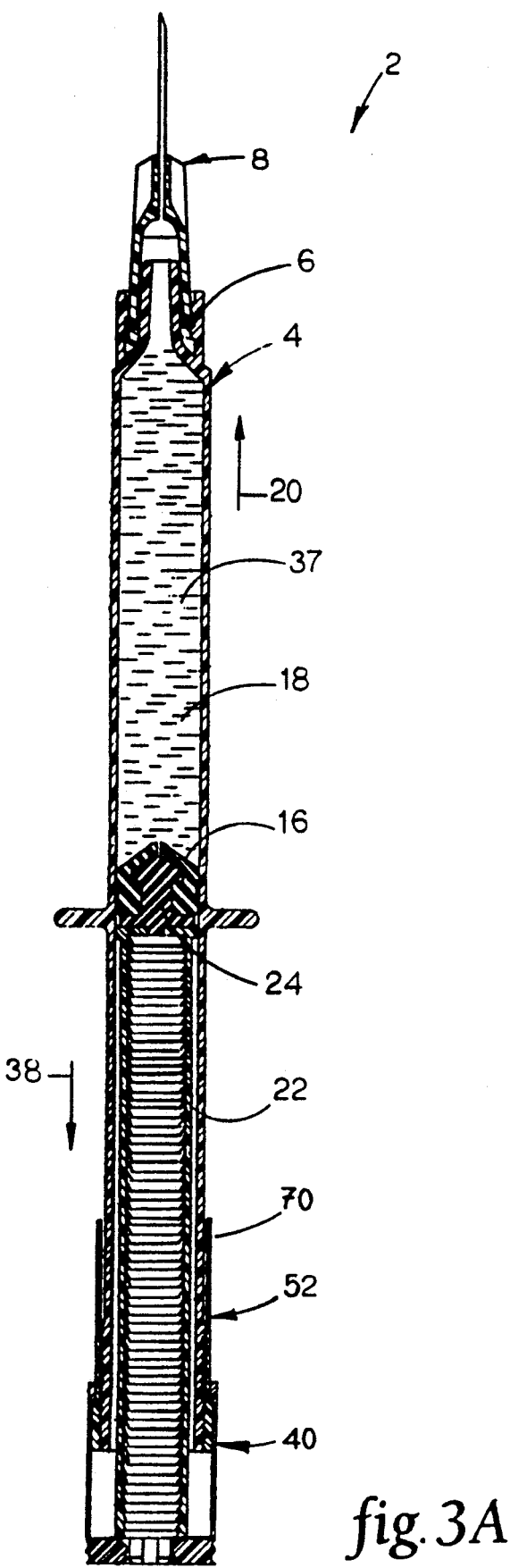
FIG. 3A is a cross-sectional view of the device shown in FIG. 1 without the dose setting key.
Figure 3B:
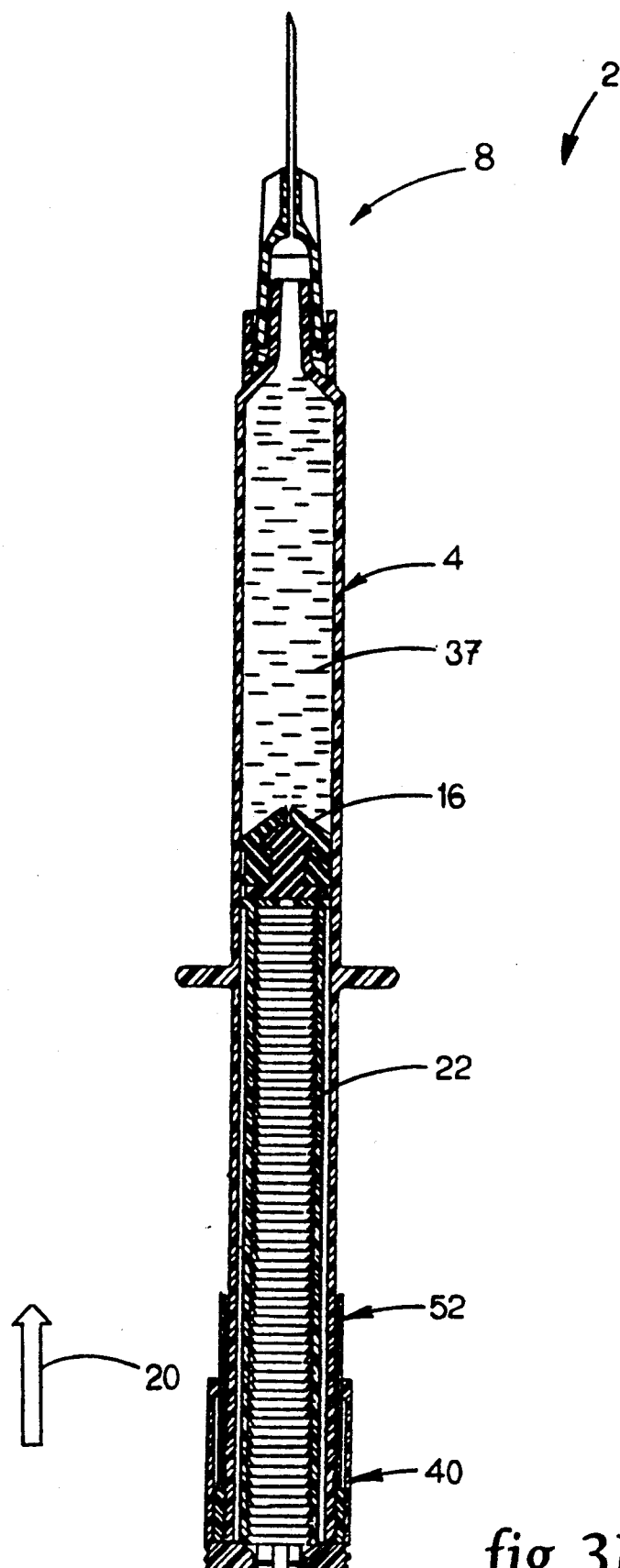
FIG. 3B shows the device of FIG. 3A after the injection stroke.
Figure 3C:
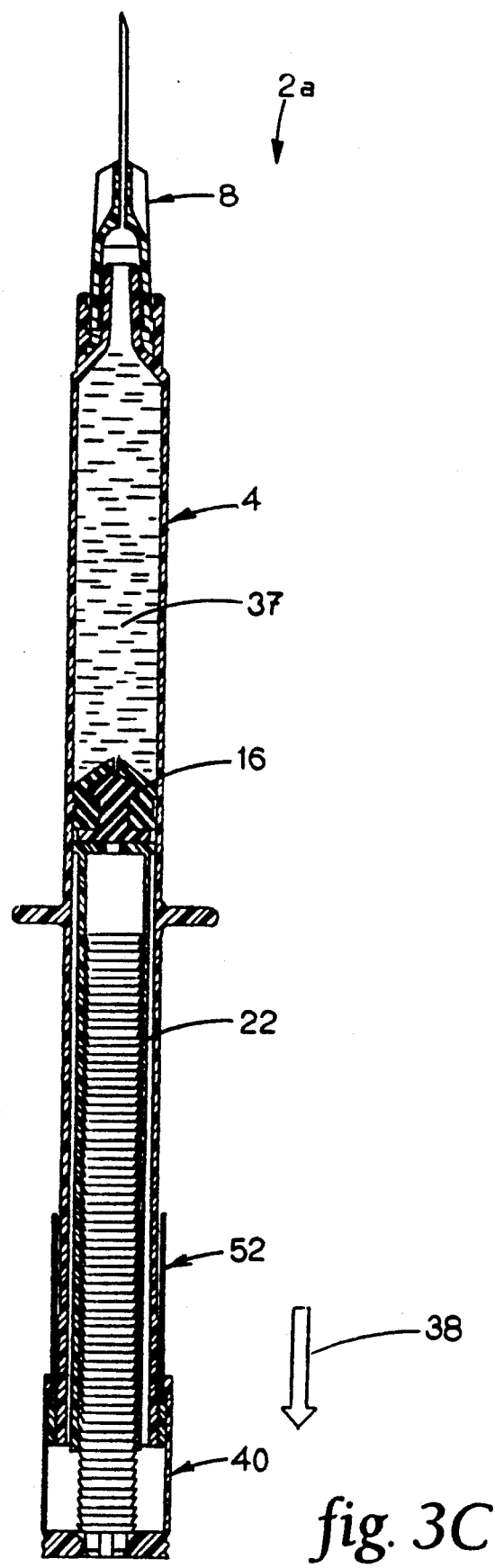
FIG. 3C shows the device of FIG. 3B after the return stroke.
Figure 4:
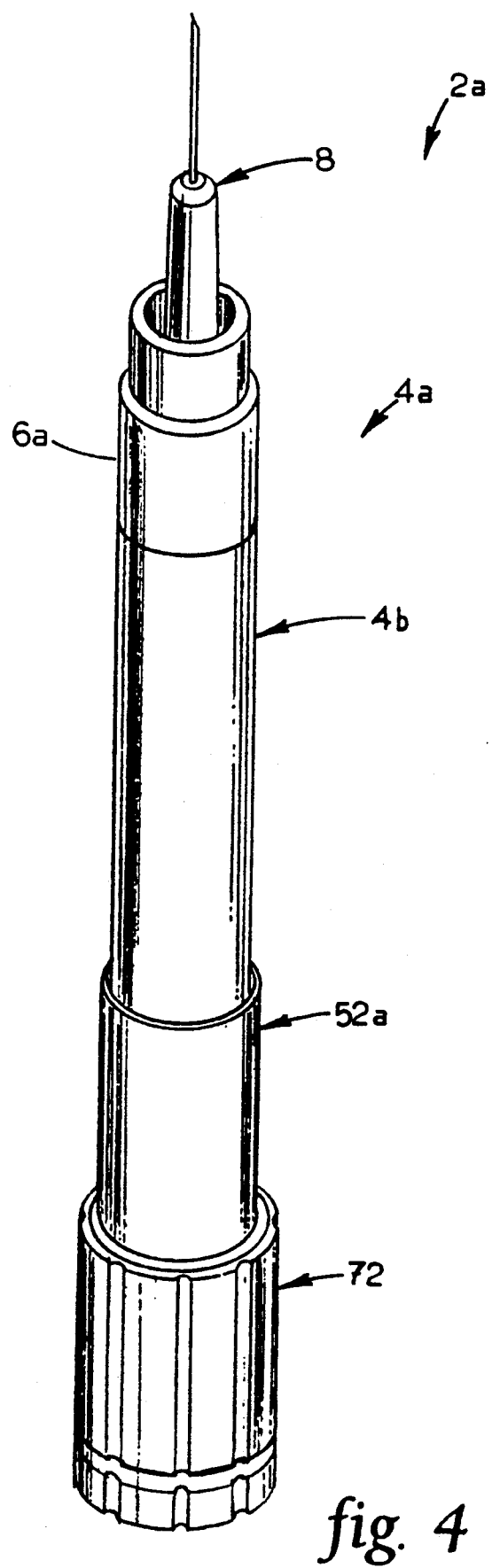
FIG. 4 is a perspective view of an alternative embodiment of the invention having a hydraulic dose repeating assembly.
Figure 5:
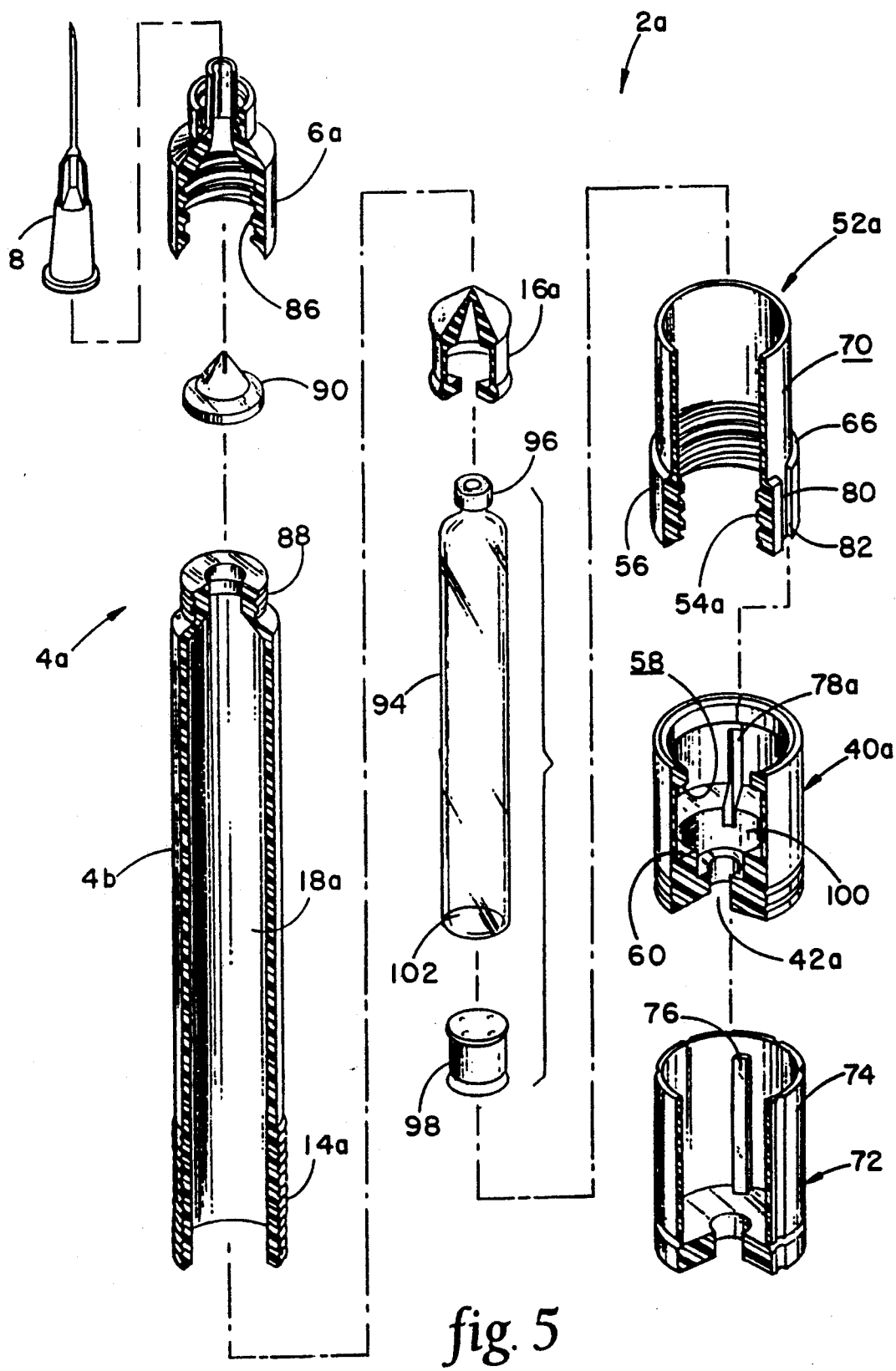
FIG. 5 is an exploded perspective view of the device shown in FIG. 4.

Dose plunger 40 is sized to fit over a cylindrical dose ring 52. Dose ring 52 has internal threads 54 sized to engage external threads 14 at proximal end 12 of barrel 4. Dose ring 52 includes a radially extending dose ring shoulder 56 sized to fit within dose plunger 40. Dose plunger 40 includes an annular return stop surface 58 and an opposed injection stop surface 60. Dose ring shoulder 56 and surface 58 are sized and positioned so that dose ring shoulder 56 limits the axial movement of dose plunger 40, thus limiting the axial movement of piston 16. Typically, dose ring 52 will be positioned with its proximal stop face 62 aligned with a proximal face 64 of barrel 4 as shown in FIG. 3A or at a position distally, that is in the direction of arrow 20, of proximal face 64 as shown in FIGS. 3B and 3C. Therefore, the distal movement of dose plunger 40 during an injection stroke, as suggested in FIG. 3B, is limited by proximal face 64 of barrel 4 when injection stop surface 60 contacts proximal face 64. The movement of dose plunger 40 in the proximal direction, that is in the direction of arrow 38, is limited by the engagement of return stop surface 58 engaging face 66 of dose ring shoulder 56. Thus, by adjusting the axial position of dose ring 52 along barrel 4, the reciprocal travel of dose plunger 40 and thus piston 16 can be adjusted. Since each stroke, assuming the position of dose ring 52 on barrel 4 is not changed, is of an equal distance, each injection will dispense an equal amount.

The engagement of threads 14, 54 is relatively tight to keep dose ring from inadvertently moving and thus maintain the proper dose. The exposed outer surface 70 of dose ring 52 is smooth to hinder user adjustment of dose ring 52 on barrel 4. To adjust the position of dose ring 52, and thus the volume of the injection, a dose setting key 72 is used. Key 72 is a cupped-shaped member having a grooved outer surface 74 for enhanced grip by the user and a radially inward extending key 76 within its interior. Key 76 is sized and positioned to pass through a similarly positioned key channel 78 formed in dose plunger 40 to engage a gap 80 formed in dose ring shoulder 56. Thus, key 76 engages surfaces 82 bounding gap 80 when one rotates key 72, thus rotating dose ring 52. Using such a key helps prevent inadvertent or unauthorized changes in the dose setting by hindering the adjustment of the position of dose ring 52 on barrel 4 without the use of key 72. If desired, additional locking figures could be used to provide further security against inadvertent or unauthorized adjustment of dose ring 52.

Assuming dose ring 52 is properly adjusted and that dose plunger 40 is in the position of FIG. 3B, the user pulls on dose plunger 40 in the proximal direction of arrow 38 until shoulder 58 engages shoulder 66. To give an injection, dose plunger 40 is driven in the distal direction of arrow 20 during an injection stroke which causes ratchet stem 28 to drive ratchet plunger 22 and piston 16 therewith in the distal direction, thus forcing pharmaceutical 37 through needle end 6 of barrel 4 and needle assembly 8.

FIGS. 4-6C illustrate an alternate embodiment of the invention shown in FIGS. 1-3C using a hydraulic dose repeating assembly as opposed to the mechanical dose repeating assembly of the first embodiment. Similar structures have like reference characters. Syringe 2a includes a two-part barrel 4a including a needle end portion 6a and a barrel portion 4b. Needle portion 6a and barrel portion 4b have mating threads 86, 88 and capture a check valve 90 between them when secured to one another. Check valve 90 is configured to permit fluid flow from the interior 18a through needle assembly 8 but not the reverse. One of the main differences between the two embodiments is that with syringe 2, the supply of pharmaceutical 37 is housed within the interior 18 of barrel 4 in the region between piston 16 and needle end 6. With syringe 2a, pharmaceutical 37 is initially contained within a cartridge 92 and is driven from the interior of the cartridge into a variable volume chamber 93, defined between the piston 16a and check valve 90 within interior 18a, as described below.

Cartridge 92 includes a cartridge barrel 94 having an open distal end 96 to which piston 16a is mounted. Piston 16a is, however, a combination piston and check valve which permits pharmaceutical 37 to pass from the interior of cartridge barrel 94 into chamber 93. Cartridge 92 also includes a floating piston 98 which will travel down the cartridge barrel 94 as pharmaceutical 37 is transferred from the interior of cartridge barrel 94 to chamber 93.

With syringe 2a, cartridge 92 in effect replaces ratchet plunger 22. Syringe 2a, dose ring 52a, dose plunger 40a and dose setting key 72a are substantially similar as the corresponding components of syringe 2. The main difference is the method by which dose plunger 40a is secured to cartridge 92. This shown in FIG. 6A. Cartridge 92 is secured to dose plunger 40a at the interface 99 between a cartridge seat 100, defined within dose plunger 40a, and the proximal end 102 of cartridge barrel 94 by a friction fit or by using an adhesive.

Figure 6A:
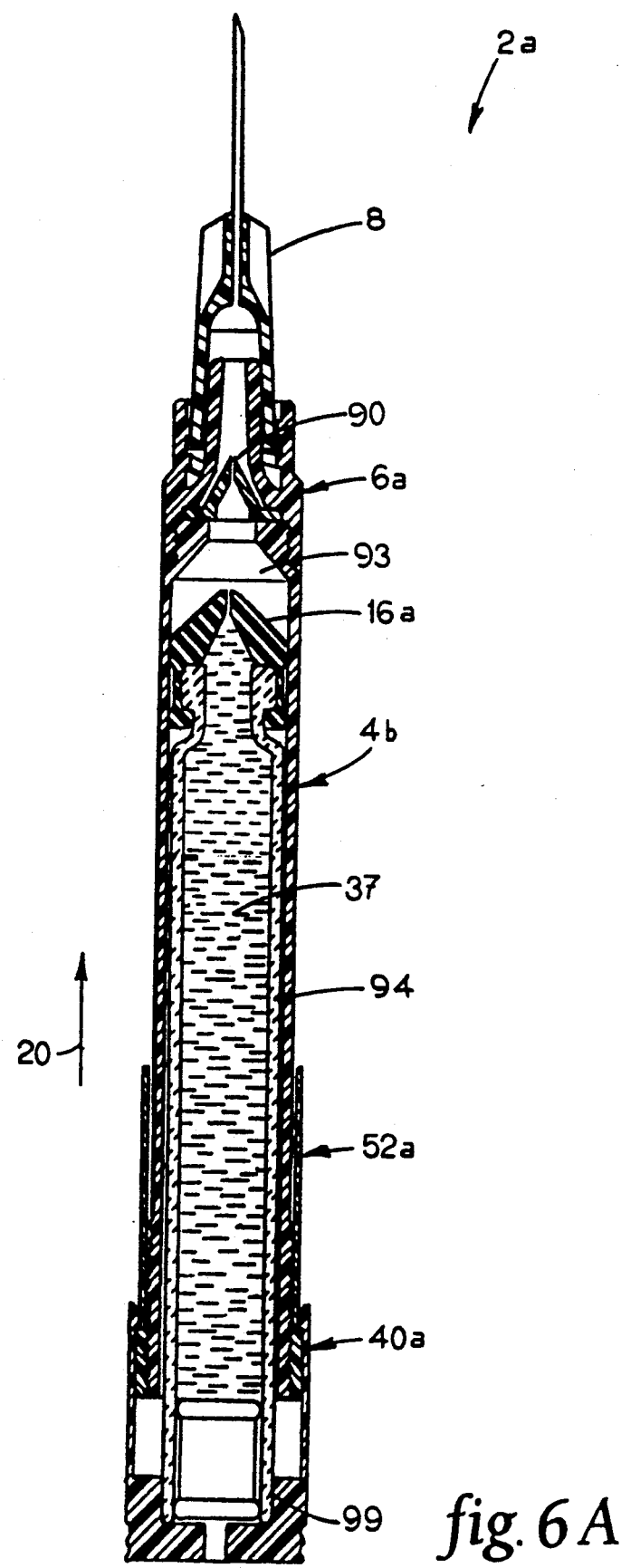
FIG. 6A is a cross-sectional view of the device of FIG. 4 without the dose setting key.
Figure 6B:
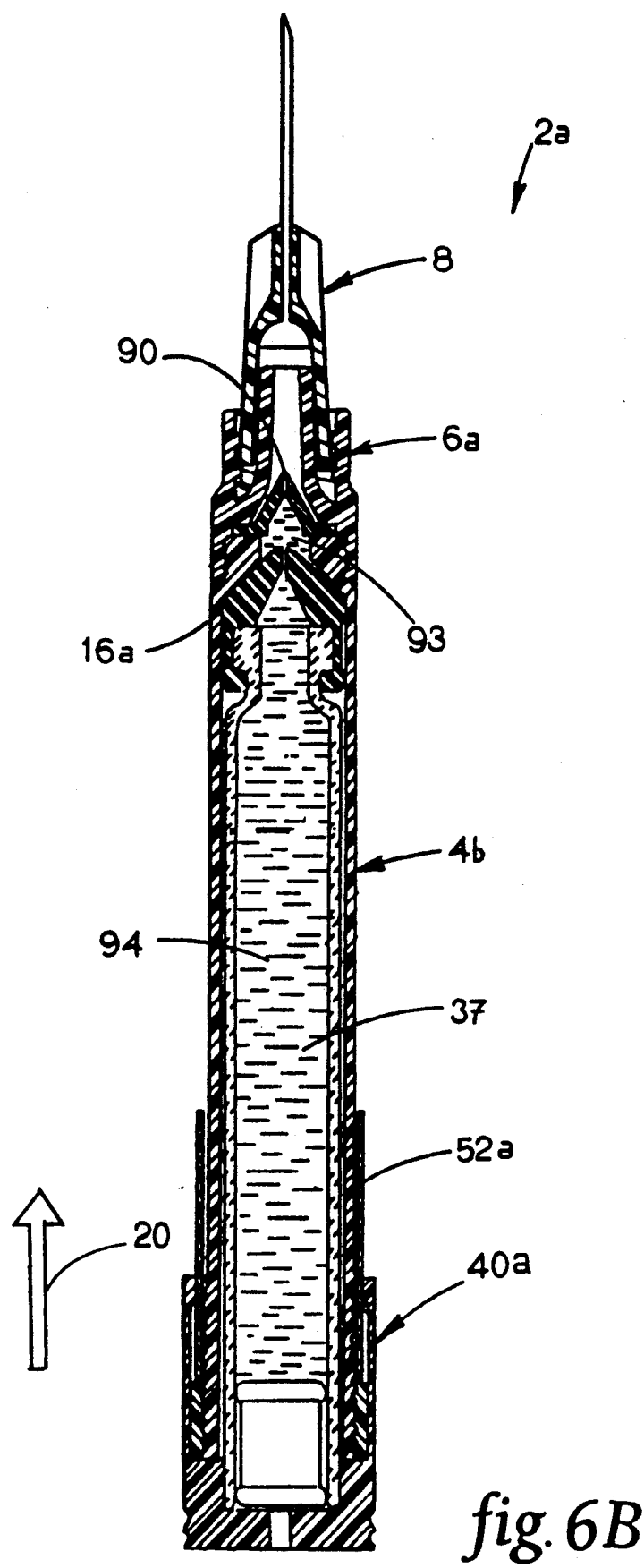
FIG. 6B shows in the device of FIG. 6A after the injection stroke.
Figure 6C:
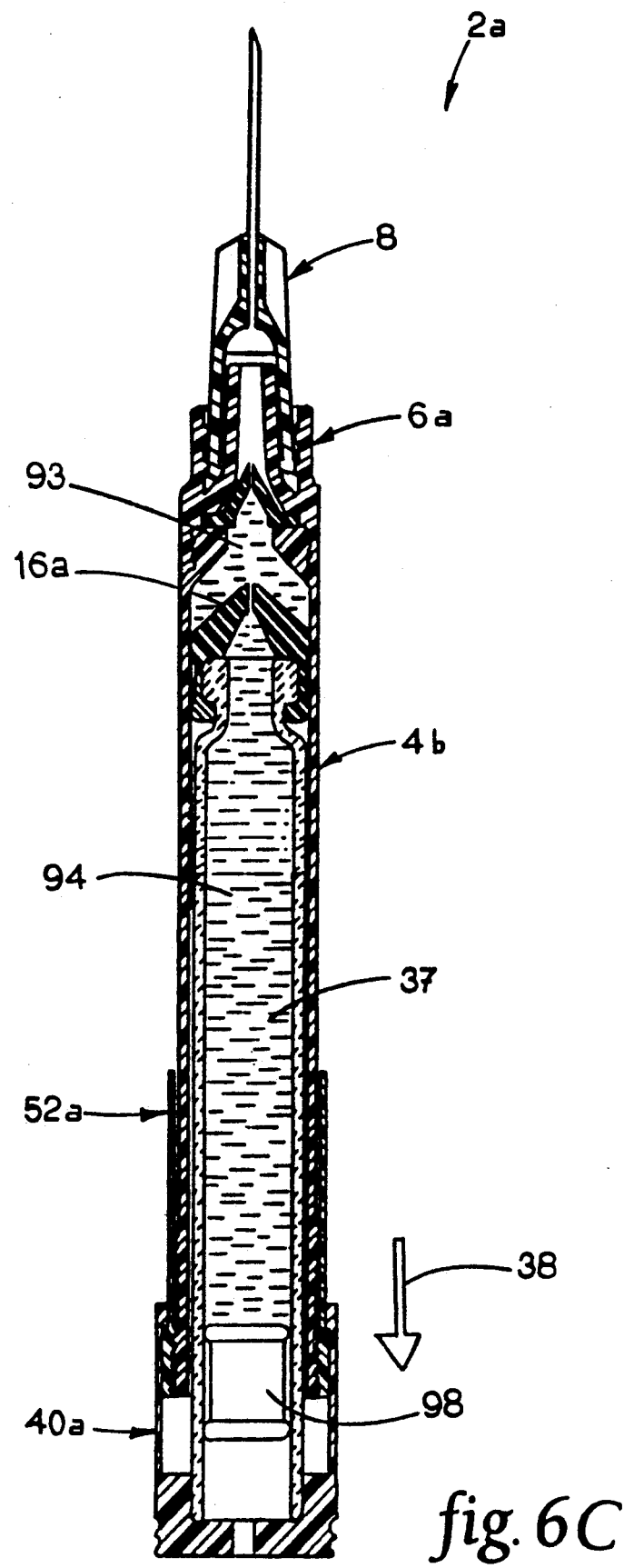
FIG. 6C shows the device of FIG. 6B after the return stroke.

FIG. 6A shows syringe 2a in a pre-use condition with no pharmaceutical within chamber 93. To prepare for making an injection, dose plunger 40a is driven in the distal direction 20 as shown in FIG. 3B. This causes cartridge 92 and piston 6a therewith to move in the distal direction 20. At least some of the air trapped in chamber 93 is forced out past check valve 90. Dose plunger 40a is then moved proximally in the direction of arrow 38 as shown in FIG. 6C. Doing so pulls cartridge 92 and combination piston and check valve 16a in the proximal direction, creating a partial vacuum within chamber 93. This partial vacuum pulls pharmaceutical 37 from cartridge 92 through combination piston and check valve 16a and into chamber 93. This reciprocal movement of dose plunger 40a is repeated until chamber 93 is filled with the pharmaceutical as suggested in FIG. 6C. Floating piston 98 permits the movement of pharmaceutical 37 from cartridge 98 into chamber 93 because it moves freely within the cartridge. Unless a maximum dose is to be injected, dose setting key 72 is used to adjust the rotary position of dose ring 52a from its position of FIG. 6A so to move dose ring 52a in the distal direction 20 to the position of FIG. 6C. An injection can now be given, the volume of which is determined by the position of dose ring 50a along barrel portion 4b for the same reasons as with the embodiment of FIGS. 1-3C.

Other modifications and variations can be made to disclose the embodiments without departing from the subject of the invention as defined in the following claims.

We claim:

1. A dose setting and repeating syringe comprising:
   a barrel having a needle end, a proximal end and a hollow interior;
   a piston within the interior for movement therein;
   a variable volume chamber defined within the interior of the barrel between the piston and the needle end for containing a liquid pharmaceutical therein; and
   a dose programming assembly including:
   a dose setting element adjustably mounted to the barrel at a chosen dose setting; and
   means for driving the piston towards the needle end equal distances during a series of injections without adjusting the dose setting element so to drive the same amount of the liquid pharmaceutical through the needle end during each injection, said amount being programmed for subsequent injections by the chosen dose setting of the dose setting element until the dose setting element is adjusted to an alternative dose setting.

2. The syringe of claim 1 wherein the dose setting element includes a dose ring threadably mounted to the proximal end of the barrel.

3. The syringe of claim 2 wherein the chosen dose setting corresponds to an axial position along the barrel.

4. A dose setting and repeating syringe comprising:
   a barrel having a needle end, a proximal end and a hollow interior;
   a piston within the interior for movement therein;
   a variable volume chamber defined within the interior of the barrel between the piston and the needle end for containing a liquid pharmaceutical therein; and
   a dose programming assembly including:
   a dose setting element adjustably mounted to the barrel at a chosen dose setting; and
   means for driving the piston towards the needle end equal distances during a series of injections so to drive the same amount of the liquid pharmaceutical through the needle end during each injection, said amount determined by the chosen dose setting of the dose setting element, wherein the piston driving means includes:
   a telescoping ratchet driver including a first ratchet element coupled to the piston and a second ratchet element ratchetly coupled to the first ratchet element and extending from said first ratchet element towards the distal end of the barrel; and
   an axially reciprocating drive element coupling the second ratchet element to the dose setting element, the axial movement of the drive element and second ratchet element therewith towards the piston being limited by the chosen dose setting of the dose setting element.

5. The syringe of claim 4 wherein the dose programming assembly includes a dose setting key means for adjusting the chosen dose setting of the dose setting element.

6. The syringe of claim 5 wherein the reciprocating drive element includes an opening formed therein, the dose setting element includes a drive surface and the dose setting key means includes a drive element sized and positioned to pass through the opening in the reciprocating drive element and engage the drive surface of dose setting element so that by manipulating said dose setting key means the chosen dose setting can be changed.

7. The syringe of claim 6 wherein the opening in the reciprocating drive element incudes an axially extending slot.

8. The syringe of claim 4 wherein the second ratchet element includes a serrated outer surface.

9. The syringe of claim 1 wherein the dose programming assembly includes:
   a cartridge containing a supply of the liquid pharmaceutical, the cartridge being housed within the interior of the barrel, the cartridge including a second piston therein, a proximal end and an open distal end, the first mentioned piston mounted to said distal end of the cartridge;
   a first check valve between the variable volume chamber and the needle end of the barrel which permits fluid flow from said chamber and through said needle end but not the reverse;
   a fluid path in the first mentioned piston coupling the liquid pharmaceutical in the cartridge to the variable volume chamber through the second check valve permitting said liquid pharmaceutical to flow from said cartridge to said chamber but not the reverse; and
   an axially reciprocating drive element coupling the cartridge, through the second piston, to the dose setting element, the reciprocating axial movement of the drive element and the cartridge and first mentioned piston therewith being limited by the chosen dose setting of the dose setting element.

10. The syringe of claim 9 wherein the second check valve and the first mentioned piston are made as a one-piece molded part.

11. A dose setting and repeating syringe comprising:
    a barrel having a needle end, a proximal end and a hollow interior;
    a piston within the interior for movement therein;
    a variable volume chamber defined within the interior of the barrel between the piston and the needle end of containing a liquid pharmaceutical therein; and
    a dose programming assembly including:
    a dose setting element adjustably mounted to the barrel at a chosen dose setting;
    means for driving the piston towards the needle end equal distances during a series of injections so to drive the same amount of the liquid pharmaceutical through the needle end during each injection, said amount determined by the chosen dose setting of the dose setting element, the piston driving means including:
    a telescoping ratchet driver including a first ratchet element coupled to the piston and a second ratchet element ratchetly coupled to the first ratchet element and extending from said first ratchet element towards the distal end of the barrel; and
    an axially reciprocating drive element coupling the second ratchet element to the dose setting element, the axial movement of the drive element and second ratchet element therewith towards the piston being limited by the chosen dose setting of the dose setting element;

a dose setting key means for adjusting the chosen dose setting of the dose setting element;

the reciprocating drive element including an opening formed therein, the dose setting element including a drive surface and the dose setting key means including a drive element sized and positioned to pass through the opening in the reciprocating drive element and engage the drive surface of dose setting element so that by manipulating said dose setting key means the chosen dose setting can be changed.

12. A dose setting and repeating syringe comprising:

a barrel having a needle end, a proximal end and a hollow interior;

a piston within the interior for movement therein;

a variable volume chamber defined within the interior of the barrel between the piston and the needle end for containing a liquid pharmaceutical therein;

a cartridge containing a supply of the liquid pharmaceutical, the cartridge being housed within the interior of the barrel, the cartridge including a second piston therein, a proximal end and an open distal end, the first mentioned piston mounted to said distal end of the cartridge;

a first check valve between the variable volume chamber and the needle end of the barrel which permits fluid flow from said chamber and through said needle end but not the reverse;

a fluid path in the first mentioned piston coupling the liquid pharmaceutical in the cartridge to the variable volume chamber through the second check value permitting said liquid pharmaceutical to flow from said cartridge to said chamber but not the reverse;

an axially reciprocating drive element coupling the cartridge to the dose setting element, the reciprocating axially movement of the drive element and the cartridge and first mentioned piston therewith, being limited by the chosen dose setting of the dose setting element; and means for driving the piston towards the needle end equal distances during a series of injections so to drive the same amount of the liquid pharmaceutical through the needle end during each injection, said amount determined by the chosen dose setting of the dose setting element.

* * * * *